US012035926B2

(12) United States Patent
Parmigiani (10) Patent No.: US 12,035,926 B2
(45) Date of Patent: Jul. 16, 2024

(54) SURGICAL INSTRUMENT FOR SCRAPING AND COLLECTING BONE PARTICLES

(71) Applicant: C.G.M. S.P.A., Correggio (IT)

(72) Inventor: Corrado Saverio Parmigiani, Correggio (IT)

(73) Assignee: META TECHNOLOGIES S.R.L., Reggio Emillia (IT)

( * ) Notice: Subject to any disclaimer, the term of this patent is extended or adjusted under 35 U.S.C. 154(b) by 486 days.

(21) Appl. No.: 17/297,869

(22) PCT Filed: Nov. 26, 2019

(86) PCT No.: PCT/IB2019/060173
§ 371 (c)(1),
(2) Date: May 27, 2021

(87) PCT Pub. No.: WO2020/115611
PCT Pub. Date: Jun. 11, 2020

(65) Prior Publication Data
US 2022/0031337 A1      Feb. 3, 2022

(30) Foreign Application Priority Data
Dec. 3, 2018   (IT) .................. 102018000010757

(51) Int. Cl.
*A61B 17/16*      (2006.01)

(52) U.S. Cl.
CPC ...... *A61B 17/1635* (2013.01); *A61B 17/1659* (2013.01)

(58) Field of Classification Search
CPC .. A61B 17/16; A61B 17/1635; A61B 17/1659
See application file for complete search history.

(56) References Cited

U.S. PATENT DOCUMENTS

| 6,110,177 A | 8/2000 | Ebner et al. |
| 2006/0173476 A1* | 8/2006 | Bradica ............. A61B 17/1635 606/179 |
| 2011/0071527 A1 | 3/2011 | Nelson et al. |

FOREIGN PATENT DOCUMENTS

| DE | 2927160 A1 | 1/1981 |
| EP | 0136079 A2 | 4/1985 |
| EP | 1829486 A1 | 9/2007 |
| WO | WO-02076307 A1 * | 10/2002 ......... A61B 17/1635 |

* cited by examiner

*Primary Examiner* — Si Ming Ku
(74) *Attorney, Agent, or Firm* — Volpe Koenig (57) ABSTRACT

A surgical instrument (10) for scraping and collecting bone particles, comprising: a gripping handle (20); a blade (30) supported by the handle (20); and a collection chamber (40) of particles scraped by the blade (30), wherein the blade (30) comprises a plurality of cutting edges (320) separated from each other.

10 Claims, 5 Drawing Sheets

FIG.7

SURGICAL INSTRUMENT FOR SCRAPING AND COLLECTING BONE PARTICLES

TECHNICAL FIELD

The present invention relates to bone tissue reconstructive and regenerative techniques in orthopedic oral maxillofacial, plastic, periodontal surgery and implantology as well as plastic techniques on bone.

More particularly, the present invention relates to a surgical instrument for scraping and collecting bone particles, or bone shavings or flakes/curls, which can be used in such tissue regeneration techniques.

BACKGROUND

In the past instruments for the collection of bone material in various areas of the skeletal structure have been developed with the aim of obtaining granules or particles of a size suitable for the biological tissue regenerative needs.

These instruments have made it possible to increase the autologous bone collection techniques and the treatment of the bone material extracted, obtaining bone granules adapted to be inserted into bone pockets for filling bone defects or for increasing skeletal structures.

In recent years, the collection methodologies have been refined thanks to the introduction of instruments on the market to remove and collect particles (flakes or shavings), by scraping, from bones, which comprise a handle that carries a scraping blade placed at its front end, and a chamber for collecting the removed material.

Said devices allow the removal of superficial cortical bone by means of a particular scraping blade, with which the instrument is provided which generates particles in the form of thin flakes or shavings, of bone which are directly collected inside the collection chamber.

The high technological level of the scraping blade allows obtaining an optimal and controllable cut with a light pressure. The collection of scraped bone particles occurs through a passage opening (slit) located at the base of the blade, which conveys them inside the collection chamber defined by a special protected tank for temporary containment. In the collection step, the bone particles are mixed with the blood to form a high bone density concentrate, ideal as a filler in regenerative techniques.

With the evolution of these regenerative techniques, the importance of some parameters of physical characterization of the bone particles has been noticed, such as for example it has been noticed that, with the same weight of collected bone particles, the greater the volume of the bone particle mass, the greater the space occupied by the same in the bone pocket to be filled and, therefore, the greater the yield of bone regeneration, and the greater the free surface of the bone particles and the greater the conversion of the bone removed into new regenerated bone in the bone pocket.

Moreover, it has been found that a further parameter of physical characterization of the bone particles to be taken into consideration is the thickness of the particles, in fact it has been noticed that too much thickness results in too rapid consumption of the implanted bone and, therefore, a low regenerative efficiency, on the contrary too high thickness results in an ineffective regeneration, because it is too slow and invasive for the patient.

Therefore, a need felt in the sector is to provide surgical instruments capable of picking up bone particles such as to maximize the desired regenerative effect, at the same time facilitating the collection operations of the personnel in charge.

It is the object of the present invention to meet such needs of the background art with a simple, functional and cost-effective solution.

In particular, an object of the present invention is to provide a surgical instrument configured for scraping and collecting bone particles, which allows scraping and collecting bone particles which together have a large free surface per weight unit, a high volume and a thickness optimized for the desired purposes.

A further object of the present invention is to provide a surgical instrument particularly convenient and functional for use by the personnel in charge and which, for example, can facilitate and guide the scraping operations, as well as allowing an efficient collection and providing the material collected in a comfortable and functional manner.

Such objects are achieved by the features of the invention disclosed in the independent claim. The dependent claims describe preferred and/or particularly advantageous aspects of the invention.

SUMMARY

The invention, in particular, provides a surgical instrument for scraping and collecting bone particles, comprising:
  a gripping handle;
  a blade supported by the handle; and
  a collection chamber of particles scraped by the blade,
  wherein the blade comprises a plurality of cutting edges separated from each other.

Thanks to this solution, it is possible to achieve the aims set out above in an effective, cost-effective and functional manner.

In particular, thanks to the multiplicity of cutting edges it is possible—with the same weight of the scraped bone particles collected in the collection chamber—to increase the volume of scraped and collected bone particles, thus increasing their ability to fill and regenerate a bone cavity.

Furthermore, thanks to the multiplicity of cutting edges it is possible—with the same weight of the scraped bone particles collected in the collection chamber—to give the scraped and collected bone particles a twisted and elongated shape, having a calibrated thickness (neither too thin nor too high) optimal for regenerative purposes.

It has also been observed that the scraped bone particles form a plurality of shavings (equal to the number of cutting edges of the blade), in particular various shavings at every movement, which having a lower thickness (with respect to the single shaving that is formed with the blade with only one cutting edge) become more twisted, thus increasing the volume of the bone particles scraped at each movement (thus increasing their filling and bone cavity regeneration capacity).

Furthermore, thanks to the multiplicity of cutting edges and their separation it is possible to define zones not cut by the blade, which with the grooves defined by the cutting edges guide the blade in a self-aligning trajectory during the scraping operation, i.e. a straight trajectory that improves the removal operations, increases the size of the scraped and collected bone particles and allows the operator a safer and more comfortable action.

Also, the presence of one or more cutting edges allows the stability of the blade to be improved (against the vibrations that incur during scraping) as well as acting as a straight line in sliding, allowing longer scraped bone particles (or curls or shavings) to be obtained (with respect to those obtained with traditional blades).

Advantageously, for these purposes the blade may comprise at least one recess interposed between two cutting edges so as to separate them.

In a preferred embodiment, the blade may comprise at least three cutting edges, of which a central cutting edge interposed between two peripheral cutting edges.

Thanks to this solution, the number and volume of the removed bone particles can be optimized.

According to an aspect of the invention, the cutting edges can lie on a same plane and are aligned along a circumferential arc.

Thanks to this solution it is possible to make a sharp and comfortable blade to make.

Advantageously, the collection chamber comprises an access opening arranged in the proximity of the cutting edges of the blade, the cutting edges being placed at the back of the access opening of the collection chamber along a scraping direction orthogonal to the plane on which the cutting edges lie in a scraping direction directed towards the handle.

According to yet another aspect of the invention, each of the cutting edges may have an apical sharp end and a curved longitudinal development along a circumferential arc portion.

Thanks to this configuration, the removal of bone particles by the blade is made optimal.

According to an aspect of the invention, the access opening may have an elastically variable section in response to a stress acting from the outside on the blade.

Thanks to this, the collection chamber is in communication with the outside only during the operation of picking up the bone material, while it is closed in the other steps and the biological material collected in the collection chamber remains therefore in sterile conditions.

The collection chamber and/or the handle may advantageously be made completely with a biologically inert plastic material, such as not to contaminate the biological material.

Moreover, the collection chamber may comprise a tub-like body closed at the top by at least one coupling surface of the handle, the collection chamber being associated with the handle with the possibility of oscillating around an oscillation axis perpendicular to the coupling surface, alternately between a closing position of the collection chamber, in which the tub-like body is aligned with the coupling surface with respect to an alignment direction parallel to the oscillation axis, and an opening position of the collection chamber, in which the tub-like body is spread apart with respect to the coupling surface.

Thanks to this solution, it is possible to make a surgical instrument able to remain in a firmly stable position against overturning when the collection tank is brought to its opening position, or is spread apart with respect to the handle to make the biological material contained in the collection chamber accessible.

BRIEF DESCRIPTION OF THE DRAWINGS

Further features and advantages of the invention will become apparent from the following description, provided by way of non-limiting example with the aid of the figures shown in the accompanying drawings.

DETAILED DESCRIPTION OF THE PREFERRED EMBODIMENTS

With particular reference to such figures, reference numeral 10 generally indicates a surgical instrument for scraping and collecting, for example manually, bone particles, or bone shavings or bone flakes/curls.

The surgical instrument 10 comprises a handle 20 which can be handled by an operator.

The handle 20 has an elongated body provided with a substantially straight longitudinal axis A, in which a proximal end of the handle 20 defines a grip 21 adapted to be gripped by a hand of the operator and an opposed free distal end.

For example, the handle 20 is made (from a monolithic body) of a plastic material, for example, it is obtained by injection molding of such a plastic material.

The handle 20, globally, has a predetermined elastic resilience which allows the handle 20 to bend flexibly, when stressed by a transverse stress (radially directed or having at least one radially directed component with respect to the longitudinal axis A) and to return to the non-deformed position when such transverse stress is lost.

In the illustrated embodiment, the handle 20 comprises a widened proximal (or rear) sector, which defines said handle grip 21 and a distal sector, which comprises the distal end itself, which has a reduced cross-section with respect to the proximal sector.

In particular, the distal sector is defined by an elongated plate-shaped body which has a first longitudinal end which is derived from the proximal sector and a second free longitudinal end, for example folded and tapered (like a tip).

The plate-like body comprises an upper outer face (shaped as desired) which is convex (or defines an extrados), and a lower inner face (which has a planar surface proximal to the first longitudinal end) and has a concave region (or defining an intrados) close to the second longitudinal end.

The terms "lower" and "upper" are used in the present description with reference to the position of the surgical instrument 10 in use configuration, wherein "lower" means facing the bone to be scraped and "upper" means turned on the side opposite to the bone to be scraped.

The handle 20, near its free distal end, carries a blade 30 configured to scrape bone particles, for example in the form of bone shavings or flakes/curls.

The blade 30 has a rigidity (high, i.e. greater than the rigidity of the bone) configures so as not to enter into resonance during the scraping operation to which it is subjected.

The blade 30 is generally made of metal, preferably stainless steel.

For example, the blade 30 is fixed, preferably in an indissoluble manner, to the free distal end of the handle 20, for example at or near it.

In particular, the blade 30 is directed downwardly to the handle 20, for example it protrudes below it (in use) by at least one radial stretch.

The blade 30 (see FIG. 6A) comprises a scraping face 31 facing the proximal end of the handle 20, or towards the grip 21 thereof.

Figure 6:
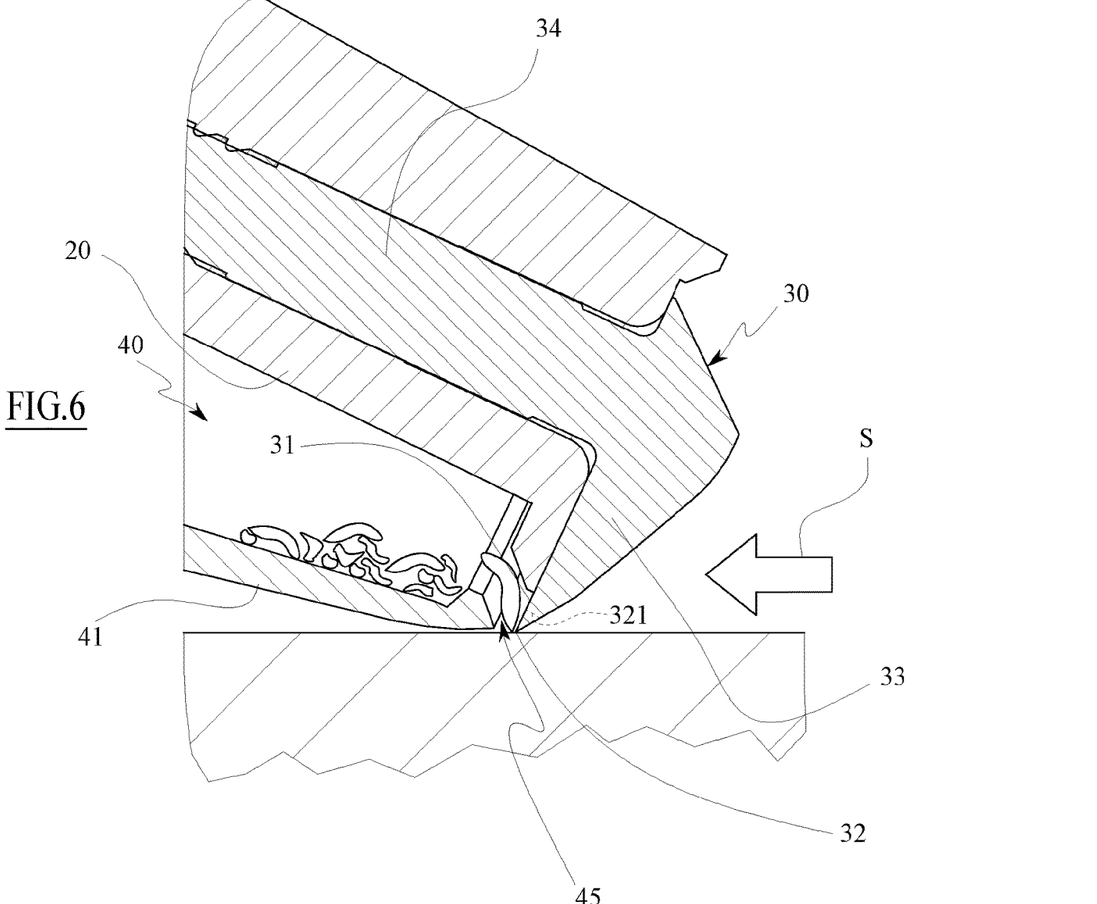
FIG. 6 is an enlarged detail of FIG. 5, illustrating the blade of the surgical instrument during a scraping operation on a bone.

In the illustrated example, the scraping face 31 is substantially planar, preferably orthogonal to the longitudinal axis A of the handle 20, in particular of the proximal sector thereof.

The scraping face 31 is a free surface of the blade 30, or protruding from the handle 20 or in any case not in contact with it or other elements of the surgical instrument 10.

The blade 30 comprises a peripheral scraping edge 32, which for example delimits (inferiorly) the scraping face 31.

The scraping edge 32 represents the portion of the blade 30 having the lowest thickness (mainly in the direction parallel to the longitudinal axis A).

The scraping edge 32 is a free edge (in use) of the blade 30, or protruding from the handle 20 or in any case not in contact with it or other elements of the surgical instrument 10, preferably facing downwards with respect to the handle 20.

The scraping edge 32, preferably, globally has a circumferential longitudinal extension.

In the illustrated example, the circumferential longitudinal development is substantially coaxial with the longitudinal axis A (which is orthogonal to the scraping face 31).

The blade 30 comprises, in the illustrated example, a discoid head 33 (e.g. monolithic), provided with an inner face, directed towards the proximal end of the handle 20, or towards the grip 21 thereof, a lower portion of which defines the said scraping face 31 and is delimited (inferiorly) by said scraping edge 32, and an opposing outer face of which faces the distal end of the handle 20 or represents the distal end of the surgical instrument 10 itself.

The blade 30 further comprises a fixing tang 34, for example cylindrical or prismatic, which is derived (in a single body) from the discoid head 33, for example from the inner face thereof, with an axis orthogonal to the scraping face 31, for example parallel and coaxial to the longitudinal axis A.

The fixing tang 34 is configured to be firmly and rigidly fixed within a (cylindrical) seat formed in the free distal end of the handle 20, for example remaining firmly constrained therewith with no possibility of movement.

In an alternative embodiment, the blade 30 may be made substantially as described in U.S. Pat. No. 6,110,177, i.e. having an arcuate scraping face, i.e. defined by a substantially semicylindrical surface with an axis orthogonal to the longitudinal axis A, and an arcuate lower edge scraping edge 32 or having a circumferential longitudinal extension substantially orthogonal to the longitudinal axis A.

In any case, according to the present invention (see FIGS. 7 and 8), the scraping (and sharp) edge 32, or the blade 30, comprises a plurality of cutting edges 320, for example two or more cutting edges 320, separated from one another, or spaced apart by a non-null distance, by an empty interspace (or at most, not scraping/not sharp).

Figure 7:
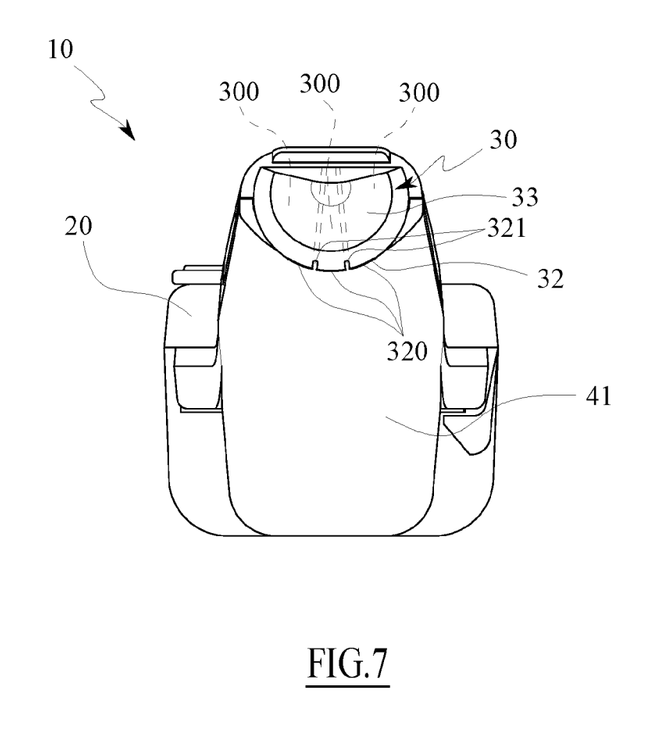
FIG. 7 is a front view of the front side of the surgical instrument.
Figure 8:
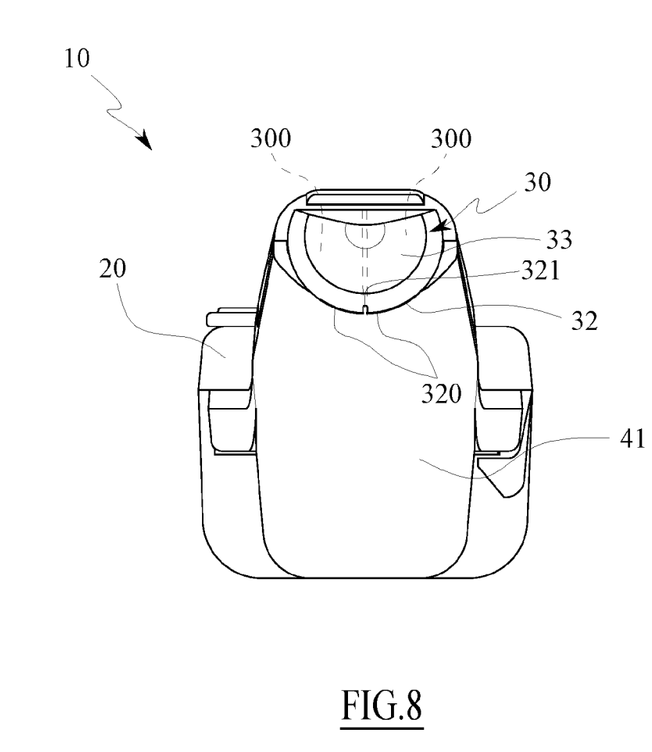
FIG. 8 is a front view of the front side of an alternative embodiment of the surgical instrument.

In practice, the scraping edge 32 is subdivided into a plurality of (circular) sectors, each of which defines a respective cutting edge 320.

Each cutting edge 320 is constituted/defined by or comprises an apex (or vertex, facing downwardly) end of the shaped edge 32 and has a longitudinal curved development along a (circular) portion of the circumferential arc (defined by the circumferential longitudinal extension of the scraping edge 32).

Preferably, the blade 30 comprises at least one recess 321 (i.e. an axially passing gap formed in the blade 30, in particular in the discoid head 33 thereof which intercepts and interrupts the scraping edge 32), which is interposed between two (adjacent) cutting edges 320, and therefore separates the same.

The recess 321 is defined by a split open at the bottom, for example longitudinal in shape with a radial longitudinal axis or in any case parallel to the scraping face 31.

The length of the recess 321 is (much) smaller than the diameter of the blade 30, in particular, it extends over a limited portion of the scraper face 31 (i.e. over a limited end portion thereof smaller than its entire area).

For example, the length of the recess 321 is comprised between 0.1 mm and 1 mm, preferably equal to 0.3 mm.

The (circumferential) width of the recess 321, which corresponds to the (non-null) distance that distances the cutting edges 320 of the blade 30, is comprised between 0.01 mm and 1 mm, preferably comprised between 0.01 mm and 0.2 mm, e.g. advantageously equal to 0.05 mm.

Thanks to such contained distance between the cutting edges 320, it is possible to maximize the quantity of bone removed at each movement obtaining, at the same time, reduced gibbosity of the scraped bone and increasing the effectiveness of the surgical instrument 10.

Each of the recesses 321 is for example obtained by cutting, e.g. electrical discharge machining or laser cutting, of the blade 30 (i.e. of a monolithic blade, in which for example the cutting edge of the blade was sharpened in advance).

Each of the cutting edges 320 is interlocked with the (single) scraping face 31, for example is joined thereto by a scraping face portion 31 cut from the recess 321.

The cutting edges 320, being preferably part of the same scraping edge 32, all lie on the same plane, defined by the plane of the scraping face 31, and lie on a same (curved) line, or a circumferential arc (defined by the circumferential longitudinal extension of the scraping edge 32), and thus they are all aligned (in a circumferential direction).

It is not excluded that the blade 30 may be obtained by joining several blades each having its own scraping edge 32 each provided with one or more cutting edges 320.

For example, it is possible to obtain a blade 30 that has a discoid head 33 obtained from a plurality of (two or three or more) sectors 300 (as indicated schematically with three broken lines in FIGS. 7 and 8), each of which has a (single) respective cutting edge 320, in particular each sector is divided from the adjacent sector by (and at) one of the aforesaid hollows 321.

In that case (as in the case in which the discoid head 33 is monolithic) it is possible to envisage the blade 30 having the fixing tang 34 in turn made of a separate body from the discoid head 33 and rigidly fixed thereto (e.g. through any permanent, semi-permanent or removable fixing technique).

In a first (and preferred) embodiment shown in FIG. 7, the plurality of cutting edges 320 of the blade 30 comprises or consists of three cutting edges 320, of which a central or main cutting edge is interposed (in a circumferential direction) between two (identical) peripheral edges.

The central cutting edge is, for example, secanting a plane of symmetry of the blade 30 passing through the longitudinal axis A, the two peripheral cutting edges are symmetrical with respect to that plane of symmetry.

In a second (and alternative) embodiment shown in FIG. 8, the plurality of cutting edges 320 of the blade 30 comprises or consists of two (identical) cutting edges 320, for example symmetrical with respect to the aforementioned plane of symmetry.

The surgical instrument 10 comprises a collection chamber 40, configured to receive the bone particles scraped by the blade 30.

The collection chamber 40 is delimited (below and laterally) by a wall 41, shaped like an elongated tub-like body and provided with a substantially straight longitudinal axis B.

The wall 41 is at least partially optically transparent.

The collection chamber 40 is made (from a monolithic body) of a plastic material, for example, it is obtained by injection molding of such a plastic material.

Advantageously, the collection chamber 40 has a proximal longitudinal end, which is closer to the proximal end of the handle 20, and a distal longitudinal end, which is closer to the distal end of the handle 20.

The wall 41, for example, copies, in plan, the elongated shape of the proximal sector of the handle 20.

In practice, the collection chamber 40 is adapted to be closed (superiorly).

In particular, in the illustrated example, the collection chamber 40 is closed (superiorly) by the handle 20, in particular by the distal sector thereof, preferably openable, so as to allow discharge of the bone particles from the collection chamber 40 collected therein.

The lower peripheral edge of the handle 20, or the distal sector thereof, is able to come into close contact with the upper edge of the wall 41.

For example, the collection chamber 40 is associated with the handle 20 with the possibility of oscillating about an oscillation axis C perpendicular to the longitudinal axis A of the handle 20 and to the longitudinal axis B of the collection chamber 40, in which the oscillation axis C is arranged in proximity to or near the proximal longitudinal end of the collection chamber 40 (and is intermediate between the proximal end of the handle 20 and the free distal end thereof).

In particular, the oscillation axis C is orthogonal to the internal (planar) face of the handle 20 (i.e., the proximal portion thereof).

The collection chamber 40 is therefore rotatably associated, by means of a hinge pin 42 coaxial to the oscillation axis C, so as to be able to alternately oscillate between a closing position of the collection chamber 40, wherein the tub-like body defined by the wall 41 is aligned in plan (below it) to the handle 20, or to the distal portion thereof, and an opening position of the collection chamber 40, wherein the tub-like body defined by the wall 41 is misaligned (in plan), that is, it is spread apart, with respect to the handle 20, or to the distal portion thereof.

In other words, in the closing position the longitudinal axes A and B, respectively of the handle 20 and of the collection chamber 40 are superimposed (in plan) and in the opening position the longitudinal axes A and B, respectively of the handle 20 and of the collection chamber 40 are spread apart, that is, they form a non-zero angle (and not a flat one).

In practice, the distal longitudinal end of the collection chamber 40, when the collection chamber 40 is in the opening position, is angularly spaced from the free distal end of the handle 20, when instead the collection chamber 40 is in the closing position, the distal longitudinal end of the collection chamber 40 is located below the free distal end of the handle 20 (at the minimum distance therefrom, or in contact therewith).

In practice, when the collection chamber 40 is in the opening position, the surgical instrument 10 is configured so as to be able to rest steadily (on a horizontal plane) on at least three misaligned and coplanar support points with the collection chamber 40 facing upwards, in which a first resting point belongs to the tub-like body defined by the wall 41 spread apart with respect to the handle, a second support point belongs to the handle 20, for example to the grip 21, and a third support point belongs to one between the handle 20 and the blade 20, for example to the handle 20 portion in the proximity of the blade 20.

The surgical instrument 10 comprises a locking assembly 50, configured to lock temporarily or in a resolvable manner on command, the collection chamber 40 in the closing position thereof.

The locking assembly 50 comprises, for example, a snap bolt element provided with a manually operated button or other known interference means.

The collection chamber 40 further comprises an access opening 45 (see FIG. 6A), which is configured to allow the entry of the bone particles scraped by the blade 30 into the volume enclosed by the collection chamber 40 (and the handle 20, when the collection chamber 40 is in the closing position).

The access opening 45 is located near the blade 30, in the example at the distal end of the collection chamber 40.

Preferably, the access opening 45 is delimited inferiorly and laterally by the wall 41 of the collection chamber 40 and above by the handle 20.

The collection chamber 40 comprises a single access opening 45 arranged in the vicinity of all the cutting edges 320 of the blade 30, so as to convey the bone particles which are individually scraped into the (same) collection chamber 40.

The cutting edges 320 of the blade 30 are located behind the access opening 45 of the collection chamber 40 along a scraping direction S (see FIG. 6A) orthogonal to the plane on which the cutting edges 320 lie, or to the plane defined by the scraping face 31 in a scraping direction (indicated in the arrow in FIG. 6A) directed towards the handle 20, that is directed towards the grip 21 thereof.

In practice, in the scraping direction, the collection chamber 40 precedes the blade 30, i.e. the scraping face 31 the cutting edges 320 of the scraping edge 32, so that the particles, in the form of shavings or flakes/curls, of bone which gradually detach from the cortical portion of the bone are conveyed into the collection chamber 40 (suitably upside down and mixed).

If the blade 30 is made substantially as described in U.S. Pat. No. 6,110,177, the access opening is arranged near the cutting edges of the blade and the cutting edges are placed behind the access opening of the collection chamber along a scraping direction parallel to the plane on which the cutting edges themselves lie, and tangential to at least one point (more backward) of the circumferential arc in a scraping direction directed towards the handle, or towards the grip thereof.

The access opening 45, in a preferred embodiment shown in the figures, has an elastically variable (open) section in response to a stress acting from the outside on the blade 30 and/or on the handle 20.

In particular, the access opening 45 is configured to alternatively switch between an open configuration, in which its open section (or passage gap) is maximum, and a closed configuration, in which its open section (or passage gap) is maximum, for example it is completely closed.

For example, at least a portion of the surgical instrument 10 is elastically deformable so as to vary the (open) section of the access opening 45 (between the open configuration and the closed configuration), in the scraping operation by the cutting edges 320 of the scraping edge 32 of the blade 30.

In particular, at least a portion of the handle 20, preferably the distal sector thereof, is elastically deformable so as to spread apart the distal sector of the handle 20 from the wall 41 which defines the collection chamber 40 when the surgical instrument 10 is pressed, with the blade 30, against the bone and vice versa, approach it when the surgical instrument 10 is not subjected to mechanical stresses.

In light of the foregoing, the operation of the surgical instrument 10 is as follows.

In use, the surgical instrument 10 is handled by gripping it by the hand by means of the handle 20, in particular and above all the grip 21 thereof; the distal sector, which comprises the free distal end of the handle 20, and the blade 30 of the surgical instrument 10, remains free from the grip of the hand.

When the scraping edge 32 comprising the cutting edges 320 of the blade 30 is pressed down against the bone surface (as illustrated in FIG. 6A), it sinks by a limited radial stretch in the cortical layer of the bone itself.

For example, by the constraining reaction offered by the bone, the access opening 45 is brought into its open configuration which allows access of the bone particles into the collection chamber 40.

At this stage, by pulling the instrument backwards in the scraping direction along the scraping direction S, with the blade 30 pressed against the bone, a scraping operation is carried out.

In every scraping operation the bone particles scraped by each of the cutting edges 320 of which the scraping edge 32 of the (single) blade 30 is consists (shown schematically in FIG. 6A as shavings) is pushed by the scraping face 31 (i.e. by each scraping face portion 31 cut from the recess 321) of the blade 30 into the collection chamber 40, through the access opening 45, which at this stage is precisely in the open configuration.

At each scraping operation, at least one bone particle (i.e. a chip or flake) for each cutting edge 320 of which the scraping edge 32 is composed, separated (longitudinally) from the bone particles scraped by one of the other edges 320 of the scraping edge 32, is detached from the bone and conveyed into the collection chamber 40.

Furthermore, the recesses 321 which subdivide the various cutting edges 320 (i.e. the inner edges thereof) allow guiding each scraping operation along a straight scraping direction S (orthogonal to the scraping face 31 of the blade).

In practice, between the non-scraped part of the bone and the recesses 321, a sort of prismatic connection is established during the scraping operation which keeps the surgical instrument under control allowing an optimal sliding on the bone and a more regular, long and defined conformation of the bone particles scraped and collected in the collection chamber 40.

When the action of the hand on the surgical instrument 10 which pushes the blade 30 against the bone ceases, the mechanical stresses on the handle 20 cease and this is relieved and returns to its natural configuration, thus closing the access opening 45 and isolating the collection chamber 40 from the external environment. The closure of the access opening 45 can be forced by a predetermined preload force created during the assembly of the components of the surgical instrument 10.

When it is necessary to discharge the bone particles collected from the collection chamber 40 it is sufficient to bring the collection chamber 40 into its opening position.

Figure 1:
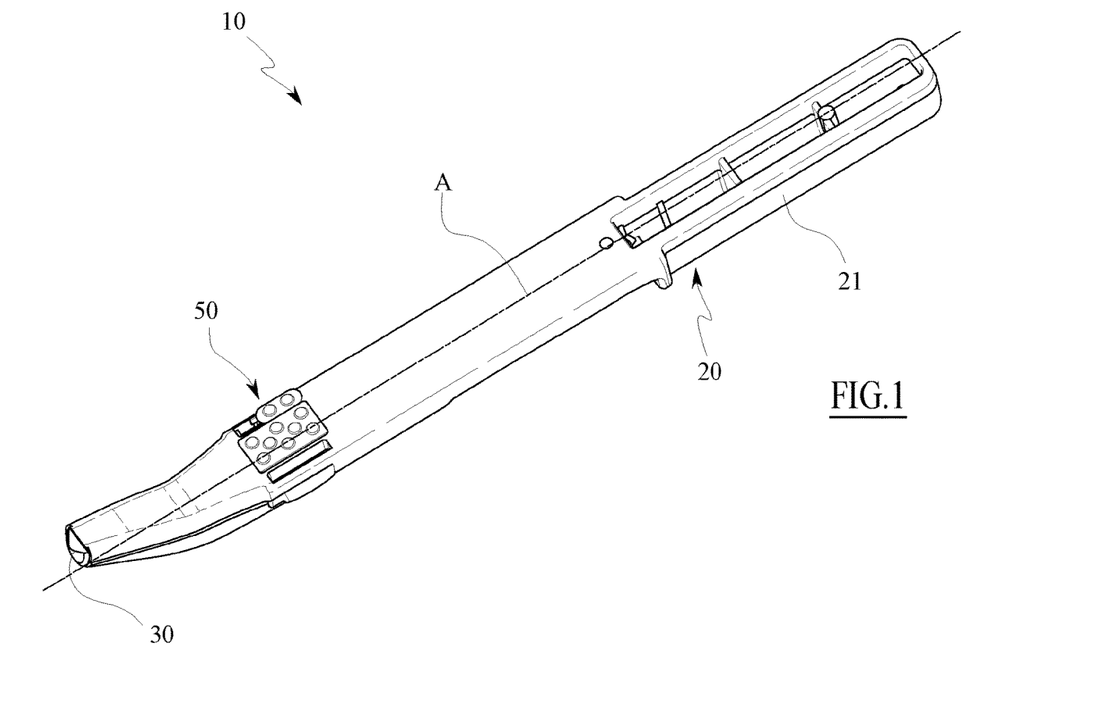
FIG. 1 is a perspective view, three quarters from above, of the surgical instrument with the collection chamber in a closed configuration.
Figures 1A, 2A:
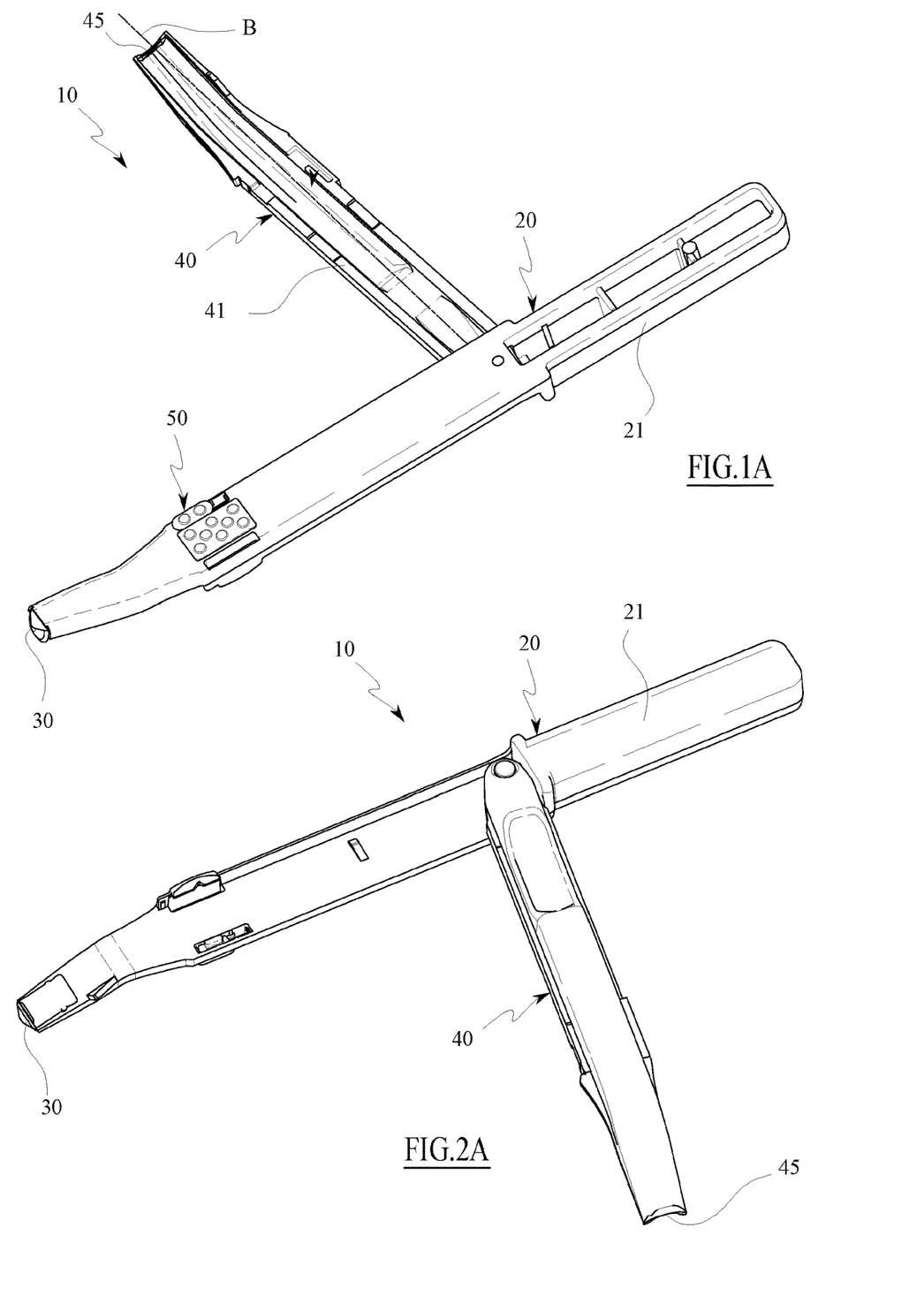
FIG. 1A is the same view as in FIG. 1, where the surgical instrument has the collection chamber in open configuration.
FIG. 2A is the same view as in FIG. 2, where the surgical instrument has the collection chamber in open configuration.
Figure 2:
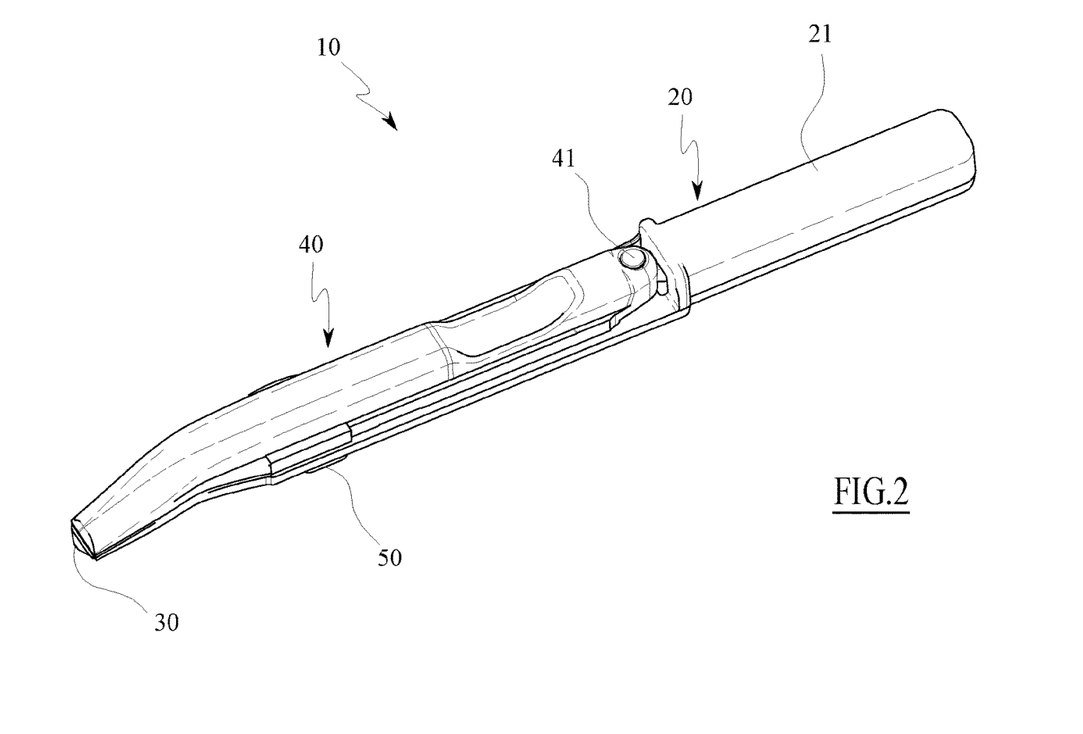
FIG. 2 is a perspective view, three quarters from below, of the subject surgical instrument with the collection chamber in a closed configuration.
Figure 3:
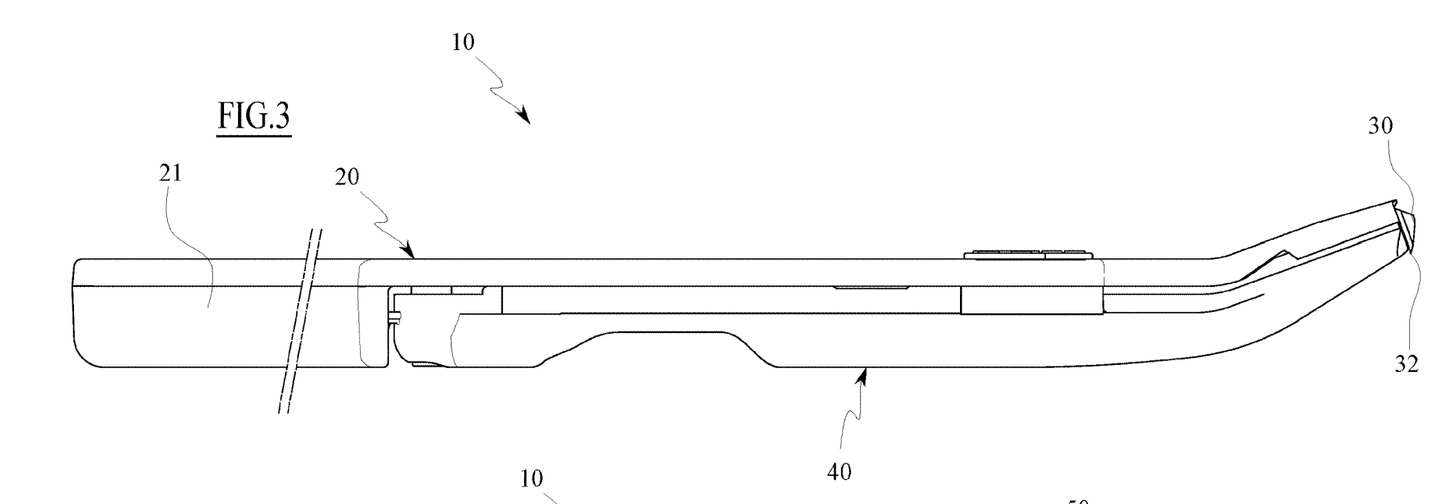
FIG. 3 is a side view of the surgical instrument with the collection chamber in a closed configuration.
Figure 4:
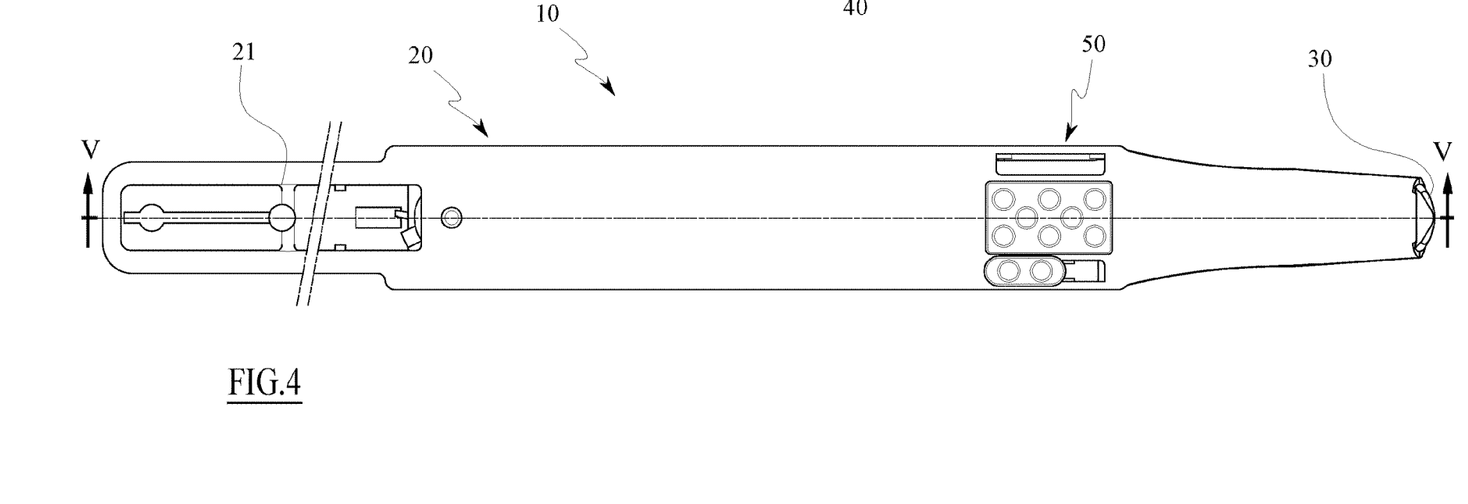
FIG. 4 is a top plan view of the surgical instrument with the collection chamber in a closed configuration.
Figure 5:
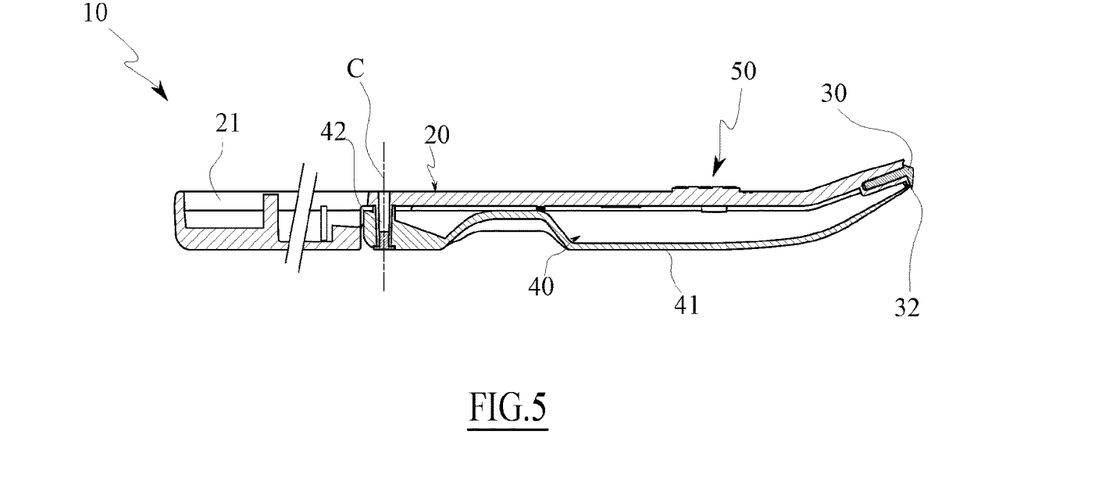
FIG. 5 is a section according to the longitudinal axial plane V-V in FIG. 4.

With the collection chamber 40 in said opening position (see FIGS. 1A and 2A), the surgical instrument 10 assumes a general "T" shape, which makes its position resting on a flat surface, for example horizontal, very stable, against overturning, in particular the position of the wall 41 defining the tub-like body of the collection chamber 40 where the biological material defined by the scraped bone particles is collected is particularly stable, upward and accessible to the operator, who may leave the surgical instrument 10 resting on a flat surface without being forced to hold it with one hand to prevent it from rolling over and losing collected bone particles.

The invention thus conceived is susceptible to numerous modifications and variations, all of which are within the scope of the inventive concept.

Moreover, all details can be replaced with other technically equivalent elements.

In practice, the materials used as well as the shapes and sizes may be any according to the requirements, without departing from the protection scope of the following claims.

The invention claimed is:

1. A surgical instrument (10) for scraping and collecting bone particles, comprising:
   a gripping handle (20);
   a blade (30) supported by the handle (20); and
   a collection chamber (40) of particles scraped by the blade (30),
   wherein the blade (30) comprises a plurality of cutting edges (320) separated from each other; and
   wherein the cutting edges (320) of the blade (30) are distanced from one another by a distance comprised between 0.01 mm and 1 mm.

2. The surgical instrument (10) according to claim 1, wherein the blade (30) comprises at least one recess (321) interposed between two cutting edges (320) so as to separate them.

3. The surgical instrument (10) according to claim 1, wherein the blade (30) comprises at least three cutting edges (320), of which a central cutting edge interposed between two peripheral cutting edges.

4. The surgical instrument (10) according to claim 1, wherein the cutting edges (320) lie on a same plane and are aligned along a circumferential arc.

5. The surgical instrument (10) according to claim 4, wherein the collection chamber (40) comprises an access opening (45) arranged the cutting edges (320) of the blade (30), the cutting edges (320) being placed at the back of the access opening (45) of the collection chamber (40) along a scraping direction (S) orthogonal to the plane on which the cutting edges (320) lie in a scraping direction directed towards the handle (20).

6. The surgical instrument (10) according to claim 1, wherein each of the cutting edges (320) has an apical sharp end and having a longitudinal curved development along a circumferential arc portion.

7. The surgical instrument (10) according to claim 1, wherein the access opening (45) has an elastically variable section in response to an external stress acting on the blade (30).

8. The surgical instrument (10) according to claim 1, wherein the collection chamber (40) comprises a tub-like body closed at a top portion thereof by at least one coupling surface of the handle (20), the collection chamber (40) being associated with the handle (20) and able to oscillate around an oscillation axis (C) perpendicular to the coupling surface, alternately between a closing position of the collection chamber (40), in which the tub-like body is aligned with the coupling surface with respect to an alignment direction parallel to the oscillation axis (C), and an opening position of the collection chamber (40), in which the tub-like body is spread apart with respect to the coupling surface.

9. The surgical instrument (10) according to claim 1, wherein the distance is comprised between 0.01 mm and 0.2 mm.

10. The surgical instrument (10) according to claim 9, wherein the distance is equal to 0.05 mm.

\* \* \* \* \*